(12) United States Patent
Dweck et al.

(10) Patent No.: US 11,672,992 B2
(45) Date of Patent: Jun. 13, 2023

(54) VALVES FOR USE IN MANUFACTURING OF IMPLANTABLE MEDICAL DEVICES

(71) Applicant: PACESETTER, INC., Sylmar, CA (US)

(72) Inventors: Gabriella Dweck, West Miami, FL (US); Adrian Baima, Woodland Hills, CA (US)

(73) Assignee: PACESETTER, INC., Sylmar, CA (US)

( * ) Notice: Subject to any disclaimer, the term of this patent is extended or adjusted under 35 U.S.C. 154(b) by 0 days.

(21) Appl. No.: 16/425,631

(22) Filed: May 29, 2019

(65) Prior Publication Data
US 2020/0376281 A1 Dec. 3, 2020

(51) Int. Cl.
*A61N 1/375* (2006.01)
*A61M 39/22* (2006.01)
*A61L 31/08* (2006.01)

(52) U.S. Cl.
CPC ........ *A61N 1/375* (2013.01); *A61F 2240/001* (2013.01); *A61L 31/08* (2013.01); *A61M 39/22* (2013.01)

(58) Field of Classification Search
CPC ........... A61F 2/04; F04B 43/08; A61M 25/06; A61M 5/48; A61M 39/22; A61M 5/31; A61N 5/00; A61N 1/375; B65D 37/00; A61K 9/22; A61L 2/20
See application file for complete search history.

(56) References Cited

U.S. PATENT DOCUMENTS

| | | | | |
|---|---|---|---|---|
| 5,030,216 A | * | 7/1991 | Theeuwes | A61K 9/0004 604/151 |
| 5,927,951 A | * | 7/1999 | Tamari | A61M 1/3639 417/476 |
| 10,130,750 B2 | | 11/2018 | Weaver et al. | |
| 10,196,186 B2 | | 2/2019 | Cox | |
| 10,295,073 B2 | | 5/2019 | Hall | |
| 10,463,796 B2 | * | 11/2019 | Thorne | A61M 5/002 |
| 2012/0095385 A1 | * | 4/2012 | Dominguez | A61F 5/0033 604/9 |
| 2013/0237923 A1 | * | 9/2013 | Ueda | A61M 39/045 604/246 |

OTHER PUBLICATIONS

R1, Duckbill Check Valve, 2016, https://www.qosina.com/in-line-duckbill-check-valve-80192 (Year: 2016).*

* cited by examiner

*Primary Examiner* — Robert S Walters, Jr.
*Assistant Examiner* — Andrew J Bowman
(74) *Attorney, Agent, or Firm* — Womble Bond Dickinson (US) LLP

(57) ABSTRACT

A valve for use in manufacturing of implantable medical devices is insertable into a bore of the medical device during a manufacturing process. The valve is configured to remain closed while the pressure differential between an internal volume of the implantable medical device and a surrounding environment is below a particular threshold and to open when the threshold is reached, thereby allowing air or other fluids to escape from the internal volume into the surrounding environment. The valves are particularly useful during certain types of coating processes that must be performed at or near vacuum and provide an effective way to prevent ingress of coating material into the internal volume of the implantable medical device.

20 Claims, 8 Drawing Sheets

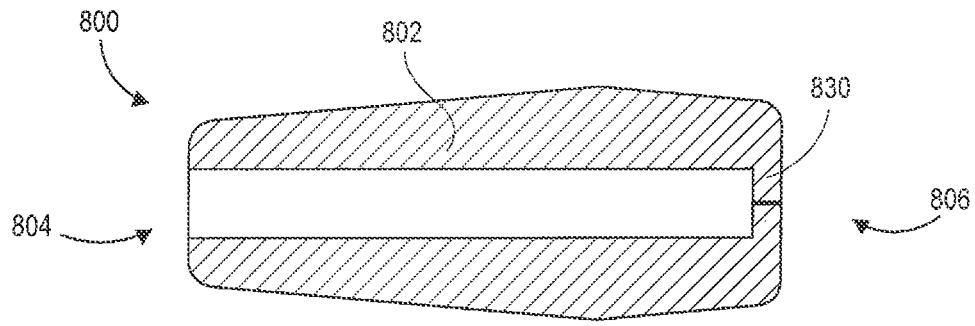
FIG. 8
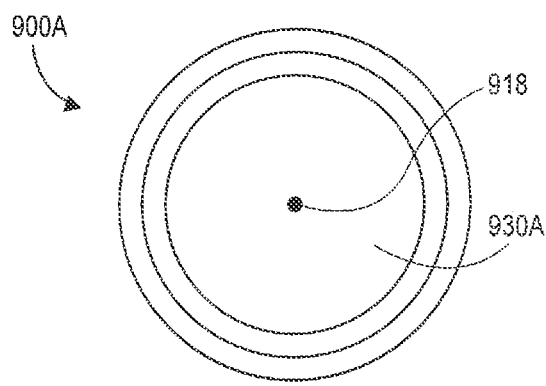
FIG. 9A
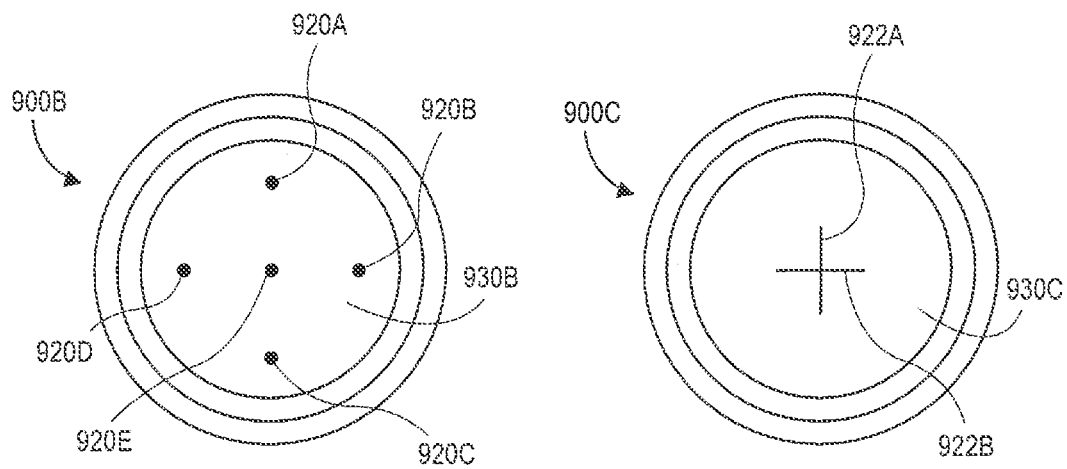
FIG. 9B
FIG. 9C

VALVES FOR USE IN MANUFACTURING OF IMPLANTABLE MEDICAL DEVICES

FIELD OF THE INVENTION

Aspects of the present invention relate to manufacturing of implantable medical devices and, in particular, to valves for use during manufacturing of implantable medical devices including coating processes.

BACKGROUND OF THE INVENTION

Implantable electronic devices (IEDs) include implantable pulse generators (IPGs) such as pacemakers and implantable cardioverter defibrillators (ICDs), which are used in the treatment of cardiac conditions, and neuromodulators or neurostimulators, which are used in chronic pain management or the actuation and control of other body systems. These IPGs commonly include a housing, feedthrus, and a connector assembly that is enclosed in a header. Electrical stimulation originating in the housing is led to the connector assembly through feedthrus. The connector assembly serves to transmit electrical signals out of the IPG and to a lead electrically connected to the connector assembly, the lead transmitting electrical signals between the IPG and patient tissue.

A header of an IPG encloses the connector assembly, which has many internal electrically conductive components such as, for example, wires, ribbon, antennas, blocks, rings, etc. The connector assembly further includes one or more connector blocks into which terminal ends of leads may be inserted. In certain IPGs, the connector blocks or adjacent structures may include setscrews that may be tightened after insertion of a terminal lead end to fix the terminal lead end.

Implantable electronic and medical devices are often coated with a biocompatible coating. Among other things, such coatings may improve corrosion/chemical resistance as compared to the substrate material, provide specific electrical properties (e.g., by having particular dielectric constants), improve thermal endurance, and provide a layer of lubrication.

It is with the foregoing in mind that the following concepts were conceived and developed.

SUMMARY OF THE DISCLOSURE

Disclosed herein is a valve for use during coating of an implantable medical device, the implantable medical device including a device bore. The valve includes a distal valve portion defining a distal valve volume and having a distal taper shaped to be inserted into the bore of the implantable medical device. The valve further includes a proximal valve portion comprising a cap, the cap including a passage in communication with the distal valve volume. The cap is biased into a closed configuration and transitions into an open configuration in response to an opening pressure differential being present across the cap.

In one implementation, the proximal valve portion has a first minimum diameter that is greater than a diameter of the device bore, and the distal valve portion has a second minimum diameter that is less than the device bore. In another implementation, the distal valve portion and the proximal valve portion are integrally formed. For example, each of the distal valve portion and the proximal valve portion may each be formed from one of silicone, polyester, or polycarbonate urethane.

Characteristics of the cap may vary between implementations. For example, the cap may be formed from a material having a stiffness from and including about 70 Shore A to and including about 90 Shore A. Also, the cap may be configured to transition into the open configuration in response to a pressure differential from about 15 in/Hg. The cap may also have a diameter of about 0.120 inches.

The passage of the proximal valve portion may also vary. For example, in certain implementations, the passage may include at least one puncture extending through the cap. In other implementations, the passage may include at least one slit extending through the cap.

In another aspect of the present disclosure, a method of manufacturing an implantable medical device including a device bore in communication with an internal volume of the implantable medical device is provided. The method includes disposing a valve in the device bore, placing the implantable medical device in a vacuum chamber defining a vacuum chamber volume, and reducing pressure within the vacuum chamber. When a low pressure is reached within the vacuum chamber, a coating is applied to the implantable medical device. When an opening pressure differential is reached between the internal volume and the vacuum chamber is reached during the pressure reducing, the valve opens to permit to flow through the valve from the internal volume to the vacuum chamber.

In one implementation, the opening differential pressure is from about 15 in/Hg.

In another implementation, the coating is applied using chemical vapor deposition (CVD). For example, the coating may be a parylene coating.

In yet another implementation, the valve includes a cap portion, opening of the valve in response to the opening pressure differential being reached includes the cap portion transitioning into an open configuration, and the fluid flow through the valve is through the cap portion. After transitioning into the open configuration, the cap portion may subsequently transition into a closed configuration in response to a pressure differential between the internal volume and the vacuum chamber falling below the opening pressure differential.

In still another implementation, the method may further include removing the valve from the device bore.

In another implementation, the implantable medical device further may include a second bore within which a second valve is disposed.

In still another aspect of the present disclosure, a valve for use during coating of an implantable medical device is provided, the implantable medical device including a device bore. The valve includes a valve body formed from silicone and having a single piece construction. The valve body includes a distal valve portion having a distal taper shaped to be inserted into the device bore, the distal valve portion defining a distal valve volume. The valve body further includes a proximal valve portion including a cap portion, the cap portion including a puncture extending through the cap portion and in communication with the distal valve volume. The cap portion is biased into a closed configuration and transitions into an open configuration in response to an opening pressure differential being present across a distal side and a proximal side of the cap portion. In the closed configuration, the puncture forms a seal, the seal preventing fluid flow from the distal valve volume through the cap portion, while in the open configuration, the puncture permits fluid flow from the distal valve volume through the cap portion. In certain implementations, the opening pressure differential is about 15 in/Hg.

BRIEF DESCRIPTION OF THE DRAWINGS

FIGS. 6A and 68 are a partial elevation view and cutaway view of an implantable medical device within which valves according to FIG. 5A are disposed.

FIG. 8 is a cross-sectional side view of an alternative valve in accordance with the present disclosure.

FIGS. 9A-9C illustrate different puncture and slit arrangements of valves in accordance with the present disclosure.

DETAILED DESCRIPTION

Implementations of the present disclosure involve valves for use during manufacturing of implantable medical devices and, in particular, valves configured to prevent ingress of coating materials into the implantable medical device during coating processes. In general, such valves function as self-sealing check valves that are biased into a closed configuration and are adapted to open when a minimum pressure differential across the valve is reached.

In one specific example, valves according to the present disclosure may be inserted into an implantable medical device/implantable electronic device prior to a coating process. The coating process may be conducted at or near vacuum. As the vacuum is formed, a pressure differential across the valve increases. When the pressure differential reaches an opening threshold for the valve, the valve opens to permit fluid to flow outward from the implantable medical device. If the pressure differential subsequently drops, the valve closes, thereby preventing backflow of coating material into the device. Applications for the valves discussed herein are broad; however, one specific example application is in preventing ingress of coating material into lead connector or other bores of an implantable medical device, such as an implantable pulse generator (IPG).

Figure 1:
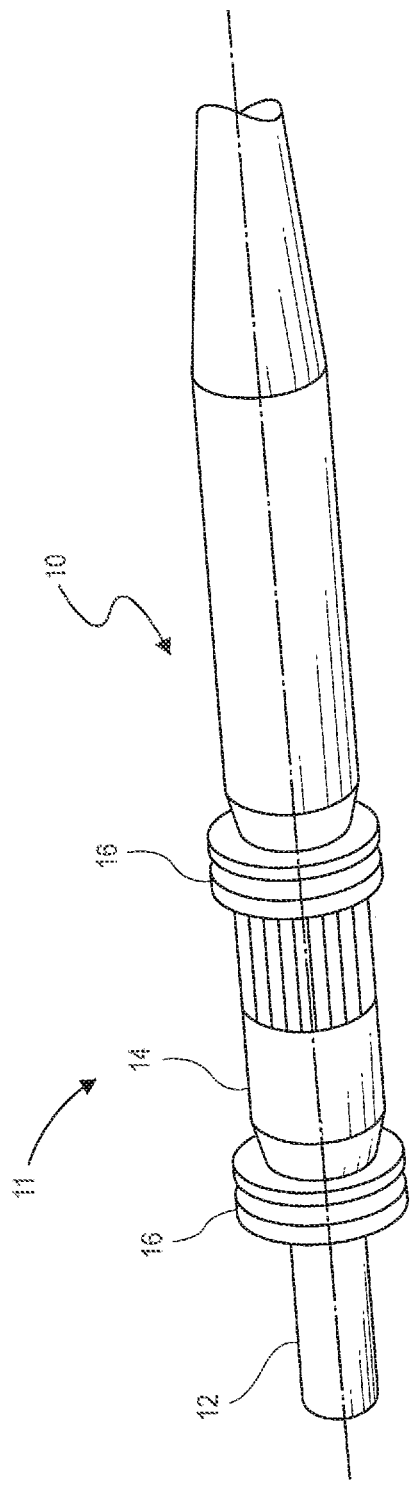
FIG. 1 is an isometric view of a proximal end portion (i.e., lead connector end) of a transvenous bipolar pacing lead.

The foregoing and other features of the present disclosure regarding implementation of the septum assemblies are provided below in further detail. However, for purposes of context, a general overview of lead connectors, IPG devices and IPG device headers is provided. It should be noted that the following overview is provided primarily for context and should not be viewed as limiting the present disclosure to applications involving any of the specific example IPG devices discussed. Rather the valves subsequently discussed herein A. Overview of Lead Connector End and IPG FIG. 1 shows a proximal end portion 10 of a transvenous, bipolar pacing lead, but is generally representative of any type of implantable lead whether in the cardiac, pain management or other medical treatment space. The diameter of such a lead may be made a sufficiently small diameter to facilitate the lead's implantation into small veins such as those found in the coronary sinus region of the heart and to allow implantation of a plurality of leads into a single vessel for multi-site or multi-chamber pacing. It should be understood, however, that other lead designs may be used, for example, multipolar leads have proximal ends portions that are bifurcated, trifurcated or have other branched configurations. While the lead whose proximal end is shown in FIG. 1 is of the bipolar variety, there are unipolar leads that carry but a single electrode, and multipolar leads that have more than two electrodes.

As is well known in the art, bipolar coaxial leads typically consist of a tubular housing of a biocompatible, biostable insulating material containing an inner multifilar conductor coil that is surrounded by an inner insulating tube. The inner conductor coil is connected to a tip electrode on the distal end of the lead. The inner insulating tube is surrounded by a separate, outer multifilar conductor coil that is also enclosed within the tubular housing. The outer conductor coil is connected to an anodal ring electrode along the distal end portion of the lead. The inner insulation is intended to electrically isolate the two conductor coils preventing any internal electrical short circuit, while the housing protects the entire lead from the intrusion of body fluids. These insulating materials are typically either silicone rubber or polyurethane. More recently, there have been introduced bipolar leads in which multifilar cable conductors contained within multilumen housings are substituted for the conductor coils in order to reduce even further the overall diameter of the lead.

The proximal lead end portion 10 shown in FIG. 1 includes a lead connector end 11 that conforms to the IS-1 standard, including a pair of coaxial spaced-apart electrical terminals including a tip terminal 12 and a ring terminal 14. The tip terminal 12 is electrically connected via of the inner conductor coil to the tip electrode at the distal end of the lead, while the ring terminal 14 is electrically connected to the anodal ring electrode via of the outer conductor coil. The tip and ring terminals of the lead connector end may each be engaged by a conductive garter spring contact or other resilient electrical contact element in a corresponding lead connector receiving bore of the header, the resilient electrical contact element being carried by a connector assembly enclosed in the header as described below. The lead connector end 11 on the proximal lead end portion 10 further comprises spaced-apart pairs of seal rings 16 for abutting against in a fluid-sealing manner the inner circumferential surface of the lead connector receiving bore of the header, thereby preventing body fluids from reaching the electrical terminals and contacts when the lead connector end 11 is plugged into the corresponding lead connector receiving bore. With the lead connector end 11 of the lead inserted in the lead connector receiving bore of the header and connector assembly, the tip and ring terminals 12 and 14 are electrically coupled via the contacts of the connector assembly and a feedthru to the electronic circuits within the hermetically sealed housing of the IPG (e.g., cardiac pacemaker, ICD, or other implantable tissue stimulation and/or sensing device such as those used in pain management, etc.).

Figure 2:
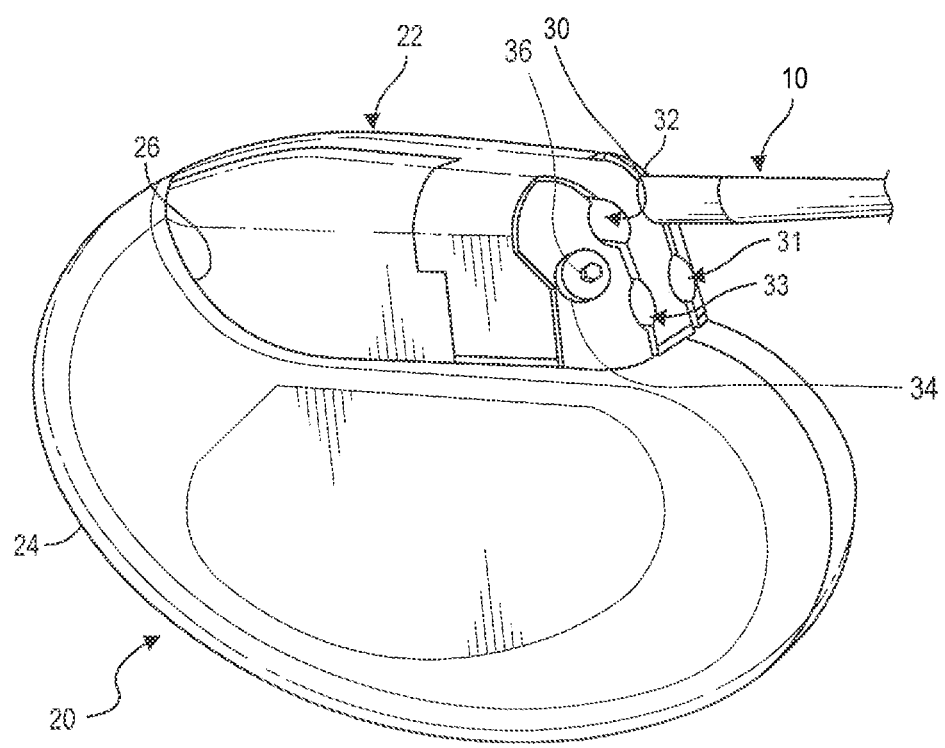
FIG. 2 is an isometric view of a cardiac pacemaker/defibrillator unit (i.e., implantable pulse generator (IPG)) incorporating connector junctions or terminals for communication with one or more electrodes.

FIG. 2 shows a multi-site or multi-chamber cardiac pacemaker/defibrillator unit that is generally representative of any type of IPG 20 incorporating a header connector assembly 22 coupled to a housing 24. The header connector assembly 22 includes a header 40 enclosing a connector assembly 42, both of which are depicted respectively in FIGS. 3, 4A and 4B discussed below. The IPG 20 includes a hermetically sealed housing 24, which is also known as a can or casing. The housing 24 encloses the electronic components of the IPG 20 with the header connector assembly 22 mounted along a top surface 26 of the housing 24.

FIG. 2 illustrates that, in some embodiments, the header connector assembly 22 may include four or more lead connector receiving bores or receptacles 30, 31, 32 and 33 for receiving the lead connector ends of four implantable leads. FIG. 2 also shows the proximal end portion 10 of a lead, wherein the lead connector end on the proximal end portion 10 of the lead is received in a corresponding receptacle 32. In other embodiments, the header connector assembly 22 includes two receptacles comprising a single pair of receptacles (i.e., receptacles 30 and 33) for receiving the proximal ends of leads such as, for example, conventional bipolar leads and/or conventional cardioverting and/or defibrillating leads. One or more setscrews 36 may be threadedly received in respective setscrew bores 34 to secure the proximal end portion 10 of the lead in the header connector assembly 22, as discussed in greater detail below.

Figure 3:
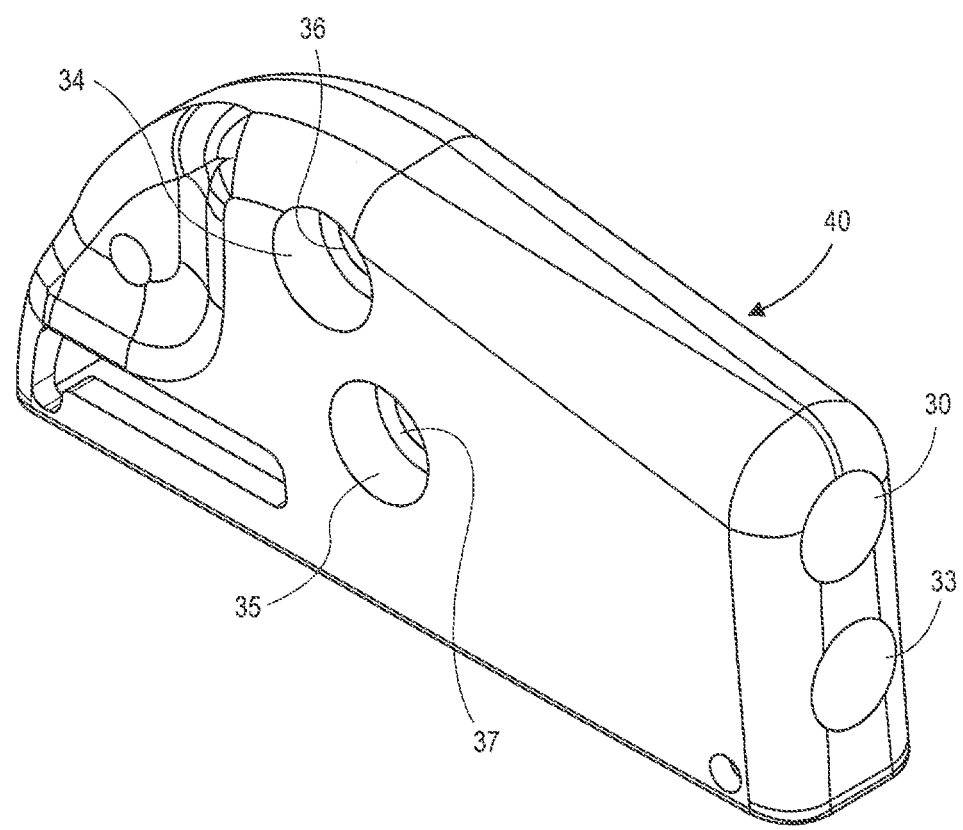
FIG. 3 is an isometric view of a representative header.
Figure 4A:
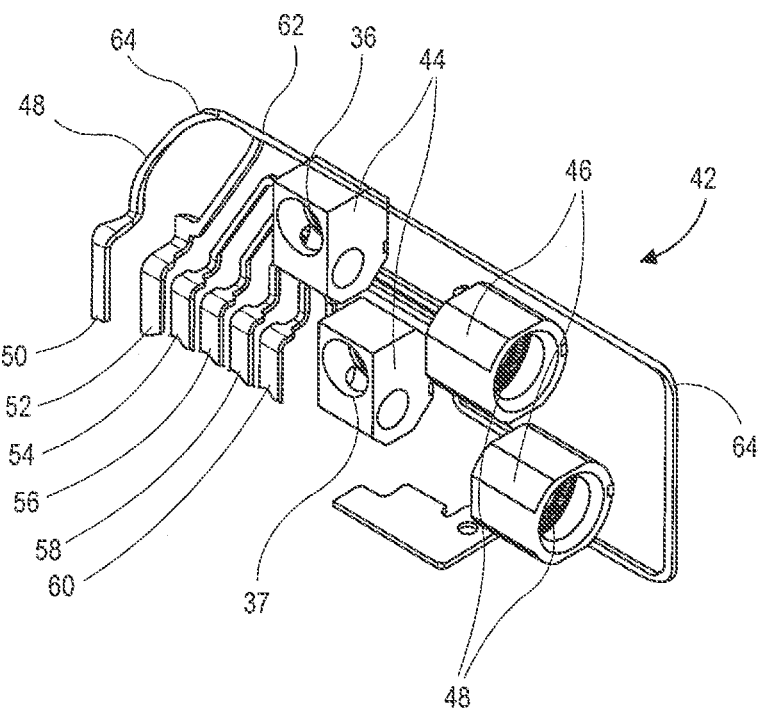
FIGS. 4A and 4B are opposite isometric views of a representative connector assembly used with the header of FIG. 3 to form a header connector assembly.
Figure 4B:
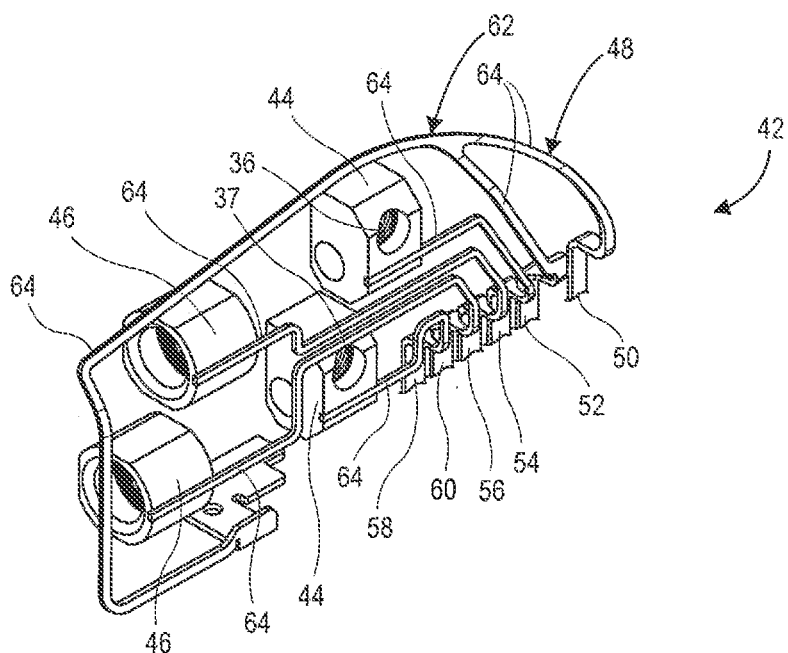

FIG. 3 is an isometric view of a representative header 40, and FIGS. 4A and 4B are opposite isometric views of a representative connector assembly 42. Unlike the header connector assembly 22 of FIG. 2, the header 40 of FIG. 3 only has a single pair of receptacles 30 and 33. However, in other embodiments, the header 40 of FIG. 3 may have two or more pairs of receptacles similar to the embodiment of FIG. 2.

Each receptacle 30, 33 is adapted to receive a proximal end of a lead, such as the proximal end potion 10 illustrated in FIG. 1. As shown in FIG. 3, the header 40 further defines a pair of setscrew bores 34, 35 corresponding to the receptacles 30, 33, respectively. Corresponding setscrews 36, 37 are disposed within the setscrew holes 34, 35 such that when proximal lead ends are fully inserted into the receptacles 30, 33, the setscrews 36, 37 may be tightened to retain the proximal lead ends within the header 40.

As illustrated in FIGS. 4A and 4B, the connector assembly 42 includes tip blocks 44 and ring blocks 46. The ring blocks 46 include spring contacts 48. Each electrical block 44 and 46 of the connector assembly 42 serves as an electrical contact of the connector assembly 42. Thus, as can be understood from FIGS. 1-4B, each tip block 44 is configured to receive and make electrical contact with the tip terminal 12 of a lead connector end 11 received in the corresponding receptacle 30, 33 of the header 40. Similarly, each ring block 46 is configured to receive and make electrical contact with the ring terminal 14 of a lead connector end 11 received in the corresponding receptacle 30, 33 of the header 40. While the connector assembly 42 of FIGS. 4A and 4B is of an IS-1 configuration, other configurations (e.g., IS-4, etc.) are used in other embodiments. While the connector assembly 42 of FIGS. 4A and 4B only depicts two pairs of blocks 44, 46, in other embodiments where the header includes more than a single pair of receptacles 30, 33 (e.g., two pairs of receptacles 30, 31, 32, 33 as indicated in FIG. 2), the connector assembly 42 will have four pairs of blocks 44, 46.

As shown in FIGS. 4A and 4B, the connector assembly 42 also includes a host of electrically conductive components including an antenna 48, an RF anchor tab 50, an RF pin tab 52, an A-tip tab 54, an A-ring tab 56, an RV-ring tab 58, an RV-tip tab 60, and a ribbon carrier 62 and other conductors 64 that extend between the various tabs and their respective electrical contacts of the connector assembly or other components thereof. In other words, as can be understood from FIGS. 4A and 4B, electrical conductor elements (e.g., wires, traces, or other electrical conductors) 64 extend between the electrical blocks 44, 46 and the respective tabs 50, 52, 54, 56, 58 and 60. Also, such conductor elements 64 may form the antenna 48 and the ribbon carrier 62.

The various tabs are welded to corresponding terminals extending from circuitry of the IPG 20 contained in the housing 24 of the IPG 20 depicted in FIG. 2 when the header connector assembly 22 is joined with the housing 24 to form the IPG 20. The connector assembly 42 is manufactured of materials and via methods known in the industry. The connector assembly 42 is cast in place, injected molded or otherwise installed into the header 40 to form the header connector assembly 22 of FIG. 2, which can be considered a first module that is then attached via a backfill or other process to a second module in the form of the housing 24. In other words, the header connector assembly 22 (i.e., first module) is attached via a backfill or other process to the housing 24 (i.e., the second module) to form the IPG 20.

B. One-Way Valve for Facilitating Coating of IPG Headers

During production of implantable medical devices, such as the IPG 20 discussed above, the implantable medical device may undergo one or more coating processes. The purpose of a particular coating may vary depending on the application for which the implantable medical device is to be used; however, in at least some applications, coatings are applied to improve the overall resistance of the implantable device to conditions within the body. Additionally, coatings may function as a layer of dry lubricant around the implantable medical device, reducing the static and/or dynamic friction coefficients of the implantable devices outer surface, thereby preventing potential irritation and damage to the tissue surrounding the implantable device.

Although coatings can provide a wide range of benefits to implantable medical devices, coating material should generally be prevented from substantially entering bores of the implantable medical device into which other components are to be inserted. One approach to preventing such infiltration during the coating process is to plug or otherwise block the bores of the implantable medical device during the coating process. However, certain coating methods are generally incompatible with simply plugging the bores.

One such coating method that can present challenges is parylene coating using chemical vapor deposition (CVD). CVD generally refers to a deposition process in which a substrate is exposed to one or more volatile precursors. The precursors react or decompose on the surface to the substrate to form a layer on the substrate. In the case of applying a parylene coating to an implantable medical device, the substrate is generally the body of the device (e.g., the header assembly 20 and the housing 24) and the precursors may be any of a range of precursors that react to form the parylene coating.

One challenge of the parylene coating process is that it is generally performed at or near vacuum. If the bores of an implantable medical device are fully plugged and sealed as a vacuum is applied, the pressure gradient across the plug may eventually increase to the point that the plug becomes unseated, allowing parylene to enter the bore.

To address the foregoing issue, implementations of the present disclosure are directed to one-way check valves that may be inserted into bores of an implantable medical device during a vacuum-based coating process. The check valves are configured to be disposed within bores or similar structures of the device during the coating process to allow venting of air from within the device.

In general, the check valves include a body and a membrane. The body has an outer shape configured to be inserted into and seal against a bore wall of the device. As vacuum is applied and pressure within the device increases relative to the surrounding environment, the membrane of the check valve opens to allow the relatively higher pressure air within the device to exit the device into the surrounding environment. Absent a sufficient pressure difference across the membrane, the membrane remains closed. Accordingly, the combination of the outer shape of the plug and the closed membrane effectively seal the bore and prevent infiltration of coating material. In other words, the one-way valve allows air to escape from within the device while sealing to prevent backflow.

Figure 5A:
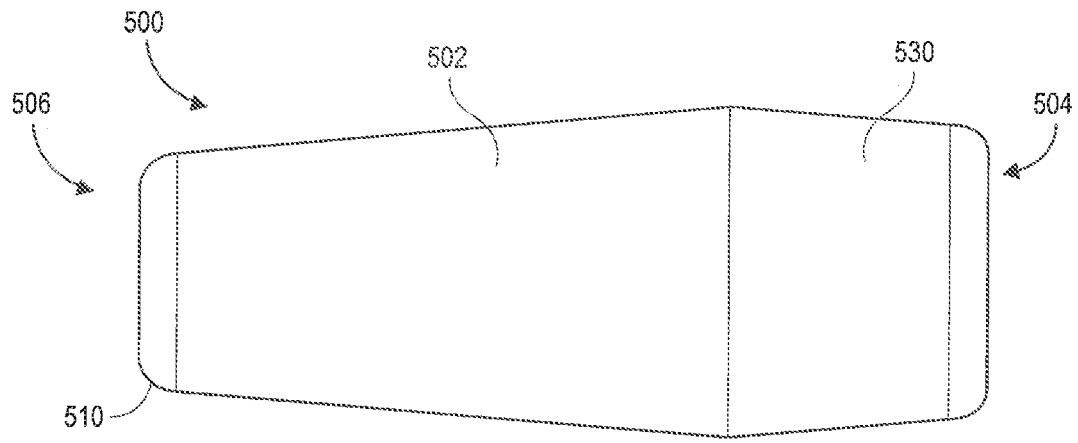
FIGS. 5A and 5B are an elevation view and cross-sectional side view, respectively, of an example valve according to an implementation of the present disclosure.
Figure 5B:
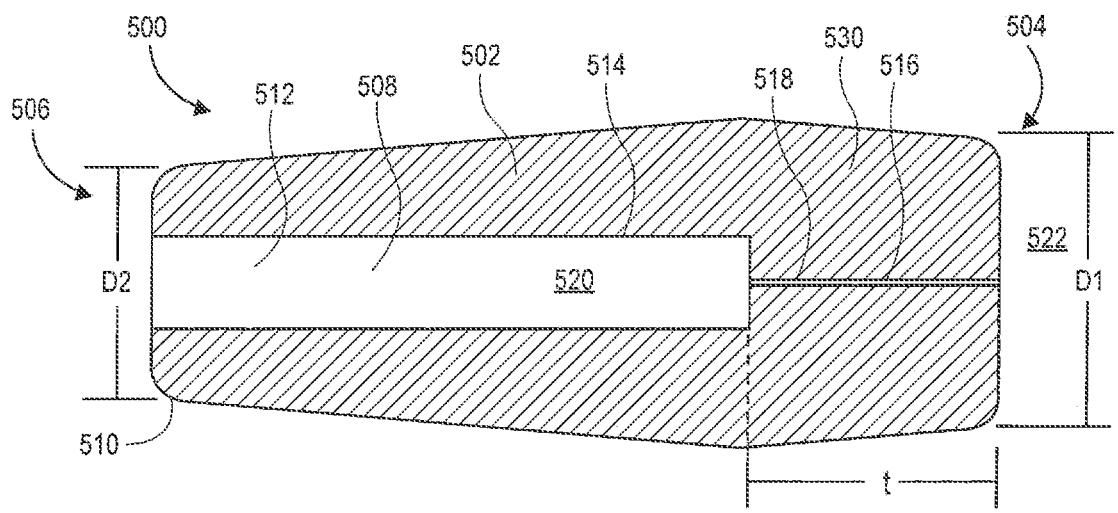

FIG. 5A is an elevation view of an example valve 500 in accordance with the present disclosure while FIG. 5B is a cross-sectional view of the valve 500. Referring first to FIG. 5A, the valve 500 includes a valve body 502 that includes each of a proximal end 504 and a distal end 506.

As previously discussed, the valve 500 is adapted to be inserted into a bore of an implantable medical device, such as an ICD, prior to coating and to prevent ingress of coating material into the implantable medical device during the coating process. To that end, the distal end 506 of the valve 500 may, in certain implementations, be tapered or otherwise include a variable shape to facilitate insertion into the bore of the implantable medical device. The distal end 506 may also include a rounded edge 510 to further facilitate insertion of the valve 500 into the bore of the implantable medical device.

To ensure proper installation of the valve 500 during use, the valve body 502 may have a first diameter D1 (shown in FIG. 5B) at the proximal end 504 that is greater than the diameter of the bore within which the valve 500 is to be disposed. As a result, the valve 500 is generally prevented from being disposed the proximal end first. The valve body 502 may also have a second diameter D2 (shown in FIG. 5B) at the distal end 506 of the valve body 502 that is less than the diameter of the bore within which the valve 500 is to be disposed, thereby facilitating insertion of the distal end 506 within the bore and proper installation of the valve 500.

The proximal end 504 of the valve 500 includes a cap 530 that provides valve functionality. The cap 530 is configured such that when in an open configuration, fluid is permitted to pass through the valve body 502. Conversely, when in a closed configuration, the cap 530 prevents fluid from passing through the valve body 502. As described below in further detail, the cap 530 transitions between the open and closed configurations in response to a pressure differential across the cap. In certain implementations, the valve 500 may be biased into the closed configuration such that when in equilibrium or below a particular opening pressure differential, backflow through the valve 500 is prevented.

Referring to the cross-sectional view of FIG. 5B, the valve 500 generally defines a passage 508 extending through the valve body 502. As illustrated, the passage 508 may include multiple sections, each having different diameters and characteristics. For example, the passage 508 of FIG. 5B includes each of a distal passage portion 512 extending from the distal end 504 into the valve body 502 and a proximal passage portion 516 extending from within the valve body 502 to the proximal end 506, including through the cap 530.

The distal passage portion 512 is illustrated in FIG. 5B as including a bore 514 extending into the valve body 502. The diameter of the bore 514 may vary in different applications of the present disclosure and may vary along the length of the distal passage portion 512. In general, however, the bore 514 is sized to remain open when the valve body 502 is disposed within an implantable medical device and to not significantly hinder movement of fluid through the distal passage portion 512.

The proximal passage portion 516 includes a hole 518 that extends from a proximal end of the distal passage portion 512 and through the cap 530 to the proximal end 504 of the valve body 502. In contrast to the bore 514, which does not substantially restrict fluid flow, the hole 518 is sized to provide valve functionality in that it is configured to alternatively permit and prevent fluid to flow through the cap 530 based on the differential pressure across the cap 530. More specifically, as differential pressure across the cap 530 (e.g., between an interior volume 520 of the bore 514 and an exterior environment 522 near the proximal end 504 of the valve 500) increases, the hole 518 is configured to expand and open. When a minimal differential pressure is reached (also referred to as the "opening pressure differential" or $\Delta P_{open}$), fluid is able to flow through the cap 530. However, if the differential pressure is below the opening pressure differential, the hole 518 remains substantially closed such that fluid is not permitted to pass through the valve body 502.

Described in an alternative manner, the hole 518 is formed through the cap 530 to substantially provide a seal at pressure differentials below the opening pressure differential, thereby preventing fluid from passing through the valve body 502. As the pressure differential increases, the cap 530 and, as a result, the hole 518 extending through the cap 530 expands, allowing fluid to pass through the valve body 502. When the pressure differential is below this opening pressure differential, the hole 518 remains substantially closed, thereby sealing the passage 508 and preventing fluid from passing through the valve body 502.

To achieve the foregoing effect, the valve 500 may be initially molded or otherwise formed to include the bore 514 but lack the hole 518. Subsequently, the hole 518 may be formed in the cap 530, such as by puncturing the cap 530 with a pin or needle, slitting the cap 530 with a razor or other blade, or otherwise forming a passage through the cap 530 without cutting away or otherwise removing substantial material from the cap 530.

It should be appreciated that the term "closed/substantially closed", or "sealed/substantially sealed" as used herein in the context of the cap 530 and the hole 518 do not necessarily require complete closure or sealing (e.g., hermetic sealing) of the cap 530. Rather, the terms closed and sealed in the context of the cap 530 and the hole 518 should be more generally understood to refer to situations in which the hole 518 presents a sufficiently tortuous path or is sufficiently obstructed that fluid is prevented from passing through the cap 530 while the differential pressure across the cap 530 remains below the opening pressure differential.

As illustrated in FIGS. 5A and 5B, the valve 500 may be a unitary component and lack any separable or moving parts. Rather, functionality of the valve 500 is imparted by the valve 500 being formed of a flexible material, such as silicone. By forming the valve 500 as a unitary assembly, manufacturing may be significantly simplified.

Figure 6A:
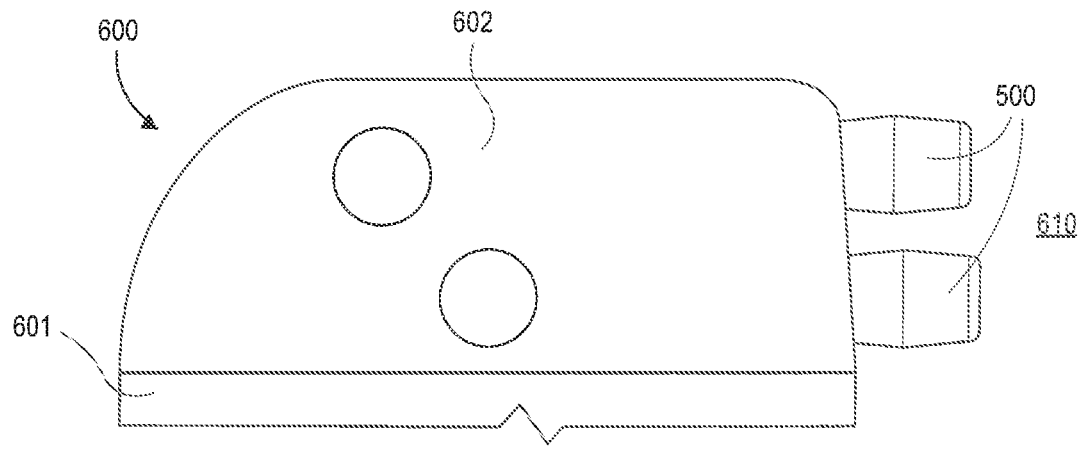
Figure 6B:
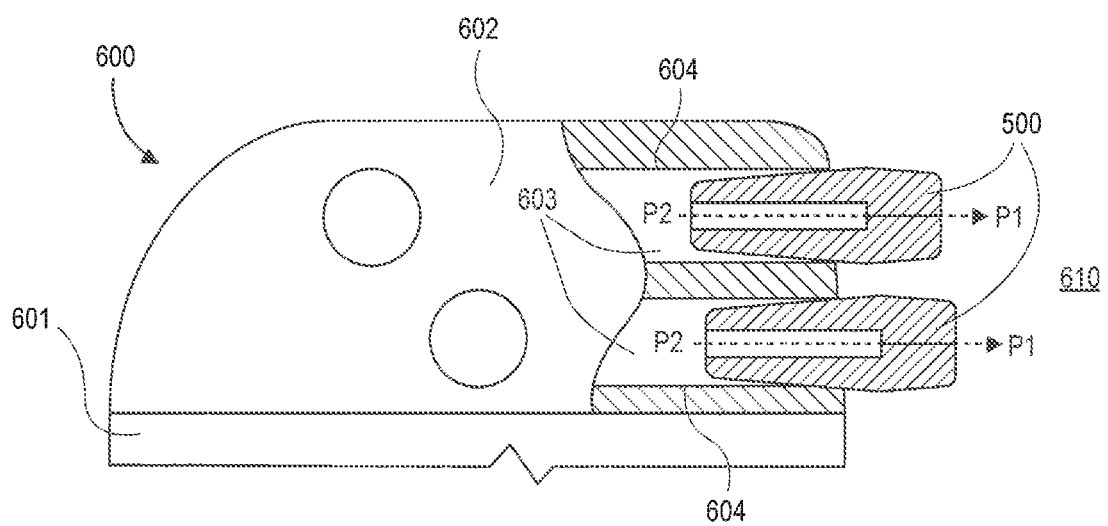

FIGS. 6A and 6B are partial views of an implantable medical device 600, with FIG. 6B including a partial cutaway of the implantable medical device 600. More specifically, the implantable medical device 600 is illustrated as an implantable cardioverter defibrillator (ICD) including a body 601 (or "can") and a header 602 coupled to the body 601. As shown in FIG. 6B, the header 602 defines an internal volume 603 that includes two bores 604, 606, which may, in at least some implementations, be adapted to receive terminal ends of leads for use with the ICD 600. Each of the bores 604, 606 are further illustrated as having respective valves 500 disposed therein.

Although illustrated in FIGS. 6A and 6B as an ICD 600, it should be appreciated that the present disclosure may be readily applied to any implantable medical device having bores or similar openings required to be blocked during coating. Similarly, while valves in accordance with the present disclosure are particularly useful in preventing ingress of coating material into lead bores (e.g., to reduce the likelihood that coating material may cover or interfere with contacts within the header), valves in accordance with the present disclosure may be more generally used to block any bore or opening during a coating process.

As previously discussed, the valves 500 may generally be used to facilitate pressure equalization during vacuum-based coating operations, such as chemical vapor deposition (CVD). In general, such processes include disposing a component to be coated within a vacuum chamber, forming a vacuum within the chamber, applying the coating, then allowing the chamber to return to atmospheric conditions before removing the coated component.

As illustrated in FIGS. 6A and 6B, the valves 500 may be inserted into the header 602 to generally prevent the coating material from entering into the header 602 and to allow pressure within the header to be released as the vacuum is formed within the vacuum chamber. More specifically, the valves 500 are generally inserted into the header 602 and seal the header 602 under ambient conditions such that an internal pressure (P2) of the header 602 is initially ambient pressure. However, once the implantable medical device 600 is inserted into the vacuum chamber and the pressure within the vacuum chamber (P1) is reduced and a pressure differential begins to form across the valves 500.

As the vacuum continues to form, the pressure differential increases until the opening pressure differential of the valves 500 is reached (e.g., (P2−P1)>$\Delta P_{open}$). At that time, the valves 500 open, permitting fluid to exit from the internal volume 603 of the header 602 to the surrounding environment 610. As fluid exits through the valves 500, the pressure differential decreases. If the pressure differential drops sufficiently, the valves 500 may once again close, thereby preventing ingress of coating material or other fluids into the internal volume 603. The foregoing process (e.g., the pressure differential across the valves 500 increasing, the valves 500 opening to permit fluid to exit the internal volume 603, and the valves 500 closing once the pressure differential is reduced) may be repeated several times as the vacuum is formed, thereby maintaining the pressure differential across the valves 500 within an acceptable range.

In certain implementations, the valves 500 may be configured such that as the pressure differential between the internal volume 603 and the vacuum chamber increases, the seal formed between the valves 500 and their respective bores 604, 606 may be reinforced. For example, greater pressure within the internal volume 603 may cause portions of the valves 500 to expand and abut the internal surfaces of the bores 604, 606 with greater force. In other implementations, air escaping from the internal volume 603 may create a suction effect that pulls the valves 500 further into their respective bores 604, 606, which, again, improves sealing.

Referring back to FIGS. 5A and 5B, the performance characteristics of the valve 500 and, more specifically, the opening pressure differential ($\Delta P_{open}$) of the valve 500, may be modified by altering various aspects of the valve 500. In one specific implementation; however, the valve 500 is generally designed to have a $\Delta P_{open}$ from and including about 15 in/Hg (~7.4 psi). In other words, the valve 500 is adapted to open when the pressure differential across the cap 530 is equal to or exceeds 15 in/Hg. In other implementations, $\Delta P_{open}$ may be other than 15 in/Hg including, without limitation, about 2 in/Hg, about 4 in/Hg, about 10 in/Hg, about 30 in/Hg, about 60 in/Hg, or about 90 in/Hg.

Different values of $\Delta P_{open}$ may be achieved in multiple ways, alone or in combination. For example, and without limitation, various factors that affect $\Delta P_{open}$ include the overall length of the hole 518, which is indicated as dimension "t" in FIG. 5B (and which generally corresponds to the thickness of the cap 520) and the material used to form the cap 530. With regards to dimension t, increasing t generally results in an increase in $\Delta P_{open}$ while decreasing t generally results in a decrease in $\Delta P_{open}$. Although dimension t may vary in different applications of the present disclosure, in at least certain implementations, t may be from and including about 0.02 in to and including about 0.06 in. In one specific implementation, t is approximately 0.04 in.

Figure 7:
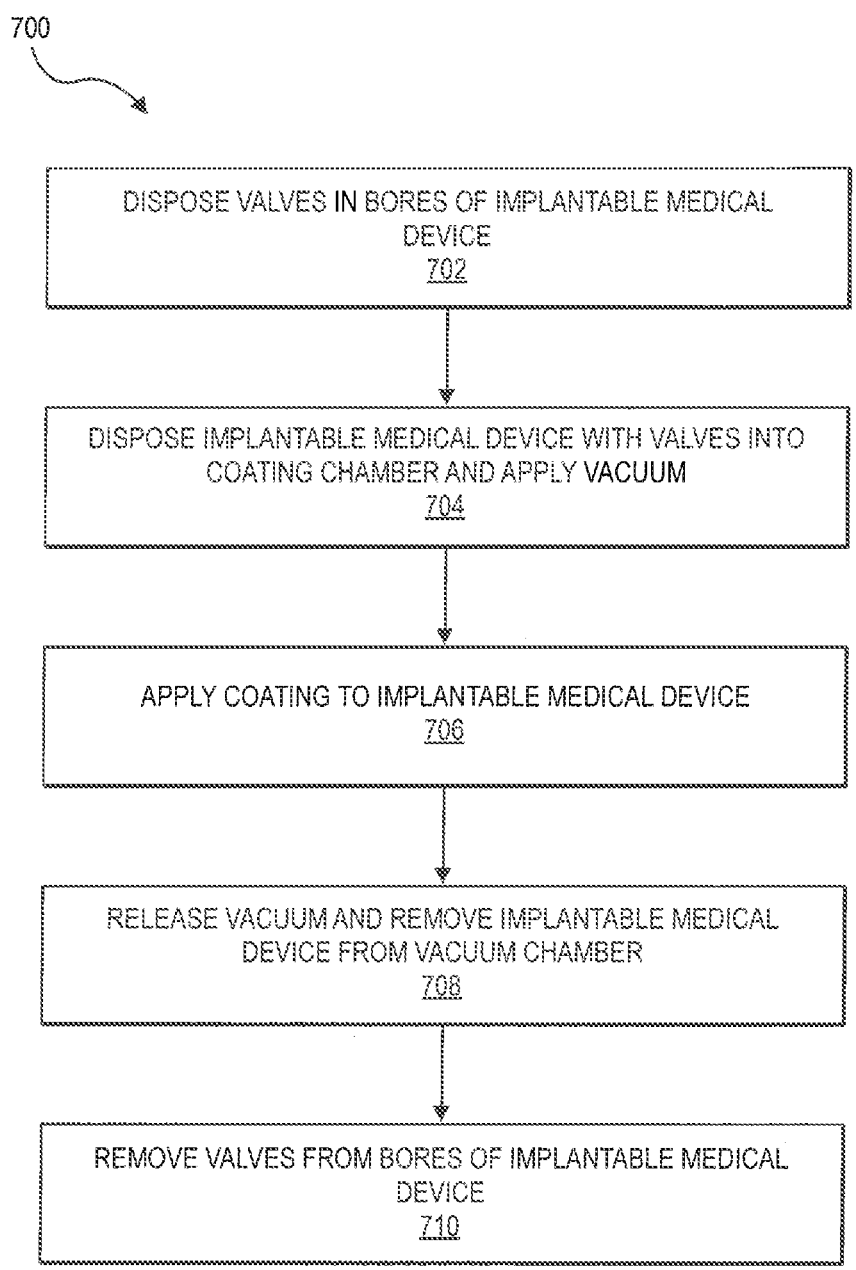
FIG. 7 is a flow chart illustrating a method of manufacturing an implantable medical device and, in particular, a method of applying a coating to an implantable medical device that makes use of the valves of FIG. 5A.

FIG. 7 is a flow chart illustrating a method 700 of manufacturing an implantable medical device using valves in accordance with the present disclosure. For purposes of the following discussion, reference is made to the valve 500 of FIGS. 5A and 5B: however, it should be appreciated that any valve in accordance with the present disclosure may be used in the methods 700.

Referring to operation 702, prior to insertion of the implantable medical device into a vacuum or other chamber, one or more valves 500 are disposed within respective bores of the implantable medical device. In one particularly implementation, at least one of the bores may correspond to a bore configured to receive the proximal end of a lead or similar electrical component.

At operation 704, the implantable medical device including the one or more valves 500 is disposed within a vacuum chamber and a vacuum is applied. As the vacuum is applied, a pressure differential forms across each of the valves. More specifically, the pressure differential results due to the valves 500 sealing an internal volume of the implantable medical device (which generally begins at ambient/atmospheric pressure) and the surrounding vacuum chamber. As a vacuum is formed, the pressure within the vacuum chamber decreases while the pressure within the implantable medical device remains substantially constant due to the seal provided by the valves 500. When the pressure differential exceeds an opening pressure differential of the valves 500, the valves open and allow air or other fluid to escape from within the implantable medical device into the surrounding chamber. Such release reduces pressure within the internal volume and, in certain cases, may result in the valves 500 closing.

As the vacuum continues to form, the pressure differential between the internal volume of the implantable medical device and the surrounding chamber volume may again increase and become sufficient to open the valves 500, releasing additional air or fluid. This process may be repeated until vacuum is reached. It should be noted that instead of cycling between open and closed configurations (e.g., "burping"), the valves 500 may initially open and remain open until a vacuum is reached. In other words, once a sufficient pressure differential is reached to open the valves, the rate of pressure change in the vacuum chamber may exceed the rate of pressure change of the internal volume of the implantable medical device such that the pressure differential does not fall below the opening pressure differential of the valves 500 until the vacuum is substantially formed. Ultimately, following formation of a vacuum within the vacuum chamber, the pressure differential between the implantable medical device and the surrounding vacuum chamber is reduced such that the valves 500 close, preventing any backflow into the implantable medical device.

At operation 706, a coating is applied to the implantable medical device. For example, parylene (or similar biocompatible coating) may be applied to the implantable medical device using a chemical vapor deposition (CVD) process. The vacuum is then released, and the coated implantable medical device is removed from the vacuum chamber (operation 708).

The valves 500 may then be removed from their respective bores (operation 710). In certain implementations, the valves 500 may be removed by simply pulling the valves 500 out of their respective bores; however, depending on the type, thickness, or other properties of the applied coating, removing the valves 500 may include cutting a layer of coating that may have formed around the valves 500. Doing so may prevent any tearing, peeling, or other damage of the coating when removing the valves 500.

FIG. 8 is a cross-sectional view an alternative implementation of a valve 800 in accordance with the present disclosure. Similar to the valve 500 of FIGS. 5A and 5B, the valve 800 includes a valve body 802 that includes each of a proximal end 804 and a distal end 806. The proximal end 804 of the valve 800 includes a cap 830 that provides valve functionality, similar to that of the cap 530 of the valve 500. However, in contrast to the cap 530 of the valve 500, the cap 830 of the valve 800 has a significantly reduced thickness (i.e., a smaller t dimension) such that, all other aspects of the valves 800 and 500 being equal, the valve 800 will generally open at a lower $\Delta P_{open}$.

Similar to the effects of dimension L, increasing the stiffness of the material used in forming the cap 530 generally results in an increase in $\Delta P_{open}$ while decreasing the rigidity or stiffness of the material generally results in a decrease in $\Delta P_{open}$. Although the stiffness of the material may vary in different applications of the present disclosure, in at least certain implementations, the cap 530 may be formed from a material having a stiffness from and including about 70 Shore A to and including about 90 Shore A. In one specific implementation, the cap 530 is formed from WACKER LR3003/80, which has a stiffness of approximately 79 Shore A. Other examples of suitable materials that may be used to form the cap 530 include, without limitation, silicone, polyester, polycarbonate urethane.

The cap 530 may be separately formed and coupled with other elements of the valve 500. For example, in certain implementations, each of a distal portion of the valve 500 and the cap 530 may be formed separately and subsequently coupled (e.g., using an adhesive, ultrasonic welding, or other suitable manufacturing technique). Alternatively, the valve body 502 may define a receptacle within which the cap 530 may be inserted or otherwise disposed. The cap 530 may also be integrally formed with the rest of the valve 500. For example, the valve 500 may cast, molded, or otherwise formed as a unitary component from the same material. Alternatively, the valve 500 may be formed using a multi-step casting or overmolding process in which different components of the valve 500 are successively formed onto each other. For example, an overmolding process may be implemented in which the cap 530 is formed from a first material during a first molding process and the remainder of the valve body 502 is formed over the cap 530 during a second molding process.

$\Delta P_{open}$ may also be modified by varying the quantity, distribution, and shape of the holes formed within the cap of the valve. For example, FIGS. 9A-9C are end views of respective valves 900A-900C, each of which includes a different cap configuration. Referring first to FIG. 9A, a first valve 900A is illustrated in which a cap 930A of the valve 900A includes a single puncture 918, similar to the hole 518 of the valve illustrated in FIGS. 5A and 5B, FIG. 9B is an end view of an alternative valve 900B including a cap 930B. Like the valve 900A of FIG. 9A, the valve 900B relies on punctures within its cap 930B to facilitate fluid flow through the cap 930B. However, in contrast to the single puncture 918 of the valve 900A of FIG. 9A, the valve 900B of FIG. 9B includes multiple punctures 920A-920E distributed about the cap 930B, with each puncture extending through the cap 930B to an internal volume of the valve 900B (e.g., similar to the bore 514 of the valve 500 shown in FIG. 5B).

FIG. 9C is an end view of a third valve 900C including a cap 930C. In contrast to the punctures of the valves 900A and 900B, the valve 900C includes a cap 930C in which multiple slits 922A, 922B have been made. The slits 922A, 922B may be formed, for example, using a razor or similar blade to that is inserted through the cap 930B to form each of the slits 922A, 922B. Alternatively, the slits 922A, 922B may be formed using an X-shaped blade punch or similar tool.

The alternative valves illustrated in FIG. 9A-9C are provided merely as examples and should not be viewed as limiting. Rather, valves in accordance with the present disclosure may include caps having any number and arrangement of punctures, slits, or similar features through which fluid may pass when the valve is in an open configuration.

C. Other Applications for One-Way Valves

Although described herein primarily for use in the context of implantable medical devices and, in particular, during coating of implantable medical devices, it should be appreciated that the one-way valves described herein may be used in other applications in which unidirectional fluid flow is desirable. For example, in one alternative application, the one-way valves disclosed herein may be incorporated into implantable shunt devices, such as implantable hydrocephalus shunts. As another example, the one-way valve design disclosed herein may be adapted for use in mechanical heart valve applications.

The foregoing merely illustrates the principles of the present disclosure. Various modifications and alterations to the described illustrative embodiments will be apparent to those skilled in the art in view of the teachings herein. It will thus be appreciated that those skilled in the art will be able to devise numerous systems, arrangements and methods which, although not explicitly shown or described herein, embody the principles of the disclosure and are thus within the spirit and scope of the present disclosure. From the above description and drawings, it will be understood by those of ordinary skill in the art that the particular embodiments shown and described are for purposes of illustrations only and are not intended to limit the scope of the present invention. References to details of particular embodiments are not intended to limit the scope of the invention.

What is claimed is:

1. A valve for use during coating of implantable medical devices, the valve comprising:
   a distal valve portion, wherein the distal valve portion has an outer shape tapering distally to a distal end including a distal edge having a distal dimension, wherein the distal valve portion defines an internal bore, and wherein the distally tapering outer shape is configured to be inserted into a device bore of an implantable medical device; and a proximal valve portion coupled to the distal valve portion and including a cap, wherein the proximal valve portion has an outer shape tapering proximally to a proximal end including a proximal edge having a proximal dimension greater than the distal dimension of the distal edge, wherein the cap includes a check valve passage that extends through the cap and that is in communication with the internal bore of the distal valve portion, wherein the internal bore is sized to remain open when a vacuum pressure differential across the valve is above or below an opening pressure differential, and wherein the check valve passage is biased into a closed configuration when the vacuum pressure differential is below the opening pressure differential and transitions into an open configuration in response to the vacuum pressure differential being above the opening pressure differential.

2. The valve of claim 1, wherein the proximal valve portion has a first minimum diameter that is greater than a diameter of the device bore and the distal valve portion has a second minimum diameter that is less than the diameter of the device bore.

3. The valve of claim 1, wherein the distal valve portion and the proximal valve portion are integrally formed.

4. The valve of claim 1, wherein the distal valve portion and the proximal valve portion are each formed from one of silicone, polyester, or polycarbonate urethane.

5. The valve of claim 1, wherein the cap is formed from a material having a stiffness from and including about 70 Shore A to and including about 90 Shore A.

6. The valve of claim 1, wherein the cap transitions into the open configuration in response to a pressure differential from and including about 12 in/Hg to and including about 17 in/Hg.

7. The valve of claim 1, wherein the cap has a thickness from and including about 0.02 in to and including about 0.06 in.

8. The valve of claim 1, wherein the check valve passage comprises at least one puncture extending through the cap.

9. The valve of claim 1, wherein the check valve passage comprises at least one slit extending through the cap.

10. A method of manufacturing an implantable medical device including a device bore in communication with an internal volume of the implantable medical device, the method comprising:

disposing a valve in the device bore, wherein the valve includes a distal valve portion, wherein the distal valve portion has an outer shape tapering distally to a distal end including a distal edge having a distal dimension, wherein the distal valve portion defines an internal bore, and wherein the distally tapering outer shape is configured to be inserted into the device bore of the implantable medical device, and a proximal valve portion coupled to the distal valve portion and including a cap, wherein the proximal valve portion has an outer shape tapering proximally to a proximal end including a proximal edge having a proximal dimension greater than the distal dimension of the distal edge, wherein the cap includes a check valve passage that extends through the cap and that is in communication with the internal bore of the distal valve portion, wherein the internal bore is sized to remain open when a vacuum pressure differential across the valve is above or below an opening pressure differential, and wherein the check valve passage is biased into a closed configuration when the vacuum pressure differential is below the opening pressure differential and transitions into an open configuration in response to the vacuum pressure differential being above the opening pressure differential;

placing the implantable medical device in a vacuum chamber defining a vacuum chamber volume and reducing pressure within the vacuum chamber to transition the check valve passage into the open configuration; and when the check valve passage is in the closed configuration, applying a coating to the implantable medical device, wherein, when the opening pressure differential is reached between the internal volume and the vacuum chamber being reached during the pressure reducing, the check valve passage opens to permit fluid flow through the valve from the internal volume to the vacuum chamber.

11. The method of claim 10, wherein the opening pressure differential is from and including about 15 in/Hg to and including about 18 in/Hg.

12. The method of claim 10, wherein the coating is applied using chemical vapor deposition (CVD).

13. The method of claim 12, wherein the coating is a parylene coating.

14. The method of claim 10, wherein the valve includes a cap portion, opening of the valve in response to the opening pressure differential being reached includes the cap portion transitioning into the open configuration, and the fluid flow through the valve is through the cap portion.

15. The method of claim 14, wherein, after transitioning into the open configuration, the cap portion transitions into the closed configuration in response to the vacuum pressure differential between the internal volume and the vacuum chamber falling below the opening pressure differential.

16. The method of claim 10, further comprising removing the valve from the device bore.

17. The method of claim 10, wherein the implantable medical device further includes a second bore within which a second valve is disposed.

18. A valve for use during coating of an implantable medical device, the implantable medical device including a device bore, the valve comprising: a valve body formed from silicone, the valve body having a single piece construction and comprising:

a distal valve portion having an outer shape tapering distally to a distal end including a distal edge having a distal dimension insertable into the device bore, the distal valve portion defining an internal bore; and a proximal valve portion comprising a cap portion, wherein the proximal valve portion has an outer shape tapering proximally to a proximal end including a proximal edge having a proximal dimension greater than the distal dimension of the distal edge, and wherein the cap portion includes a check valve puncture extending through the cap portion and in communication with the internal bore, wherein:

the internal bore is sized to remain open when a vacuum pressure differential across the valve is above or below an opening pressure differential, the check valve puncture is biased into a closed configuration and transitions into an open configuration in response to the vacuum pressure differential being above the opening pressure differential across a distal side and a proximal side of the cap portion, in the closed configuration, the check valve puncture forms a seal, the seal preventing fluid flow from the internal bore through the cap portion, and in the open configuration, the check valve puncture permits fluid flow from the internal bore through the cap portion.

19. The valve of claim 18, wherein the opening pressure differential is about 15 in/Hg.

20. The valve of claim 18, wherein the opening pressure differential is from and including about 12 in/Hg to and including about 17 in/Hg.

* * * * *